US010519522B2

(12) United States Patent
Theoleyre et al.

(10) Patent No.: US 10,519,522 B2
(45) Date of Patent: Dec. 31, 2019

(54) METHOD FOR PURIFYING OSES WITHOUT ADJUSTING PH (71) Applicant: CENTRALESUPELEC, Gif sur Yvette (FR)

(72) Inventors: Marc-Andre Theoleyre, Paris (FR); Julien Lemaire, Reims (FR)

(73) Assignee: CENTRALESUPELEC, Gif Sur Yvette (FR)

( * ) Notice: Subject to any disclaimer, the term of this patent is extended or adjusted under 35 U.S.C. 154(b) by 241 days.

(21) Appl. No.: 15/523,377

(22) PCT Filed: Oct. 30, 2015

(86) PCT No.: PCT/FR2015/052940
§ 371 (c)(1),
(2) Date: Apr. 29, 2017

(87) PCT Pub. No.: WO2016/066978
PCT Pub. Date: May 6, 2016

(65) Prior Publication Data
US 2017/0247770 A1 Aug. 31, 2017

(30) Foreign Application Priority Data
Oct. 31, 2014 (FR) ..................................... 14 60484

(51) Int. Cl.
C13K 13/00 (2006.01)
B01D 61/42 (2006.01)
(Continued)

(52) U.S. Cl.
CPC .......... C13K 13/002 (2013.01); B01D 61/027 (2013.01); B01D 61/04 (2013.01);
(Continued)

(58) Field of Classification Search
CPC .......... C13K 1/04; C13K 1/00; C13K 13/002; B01D 61/422
See application file for complete search history.

(56) References Cited

U.S. PATENT DOCUMENTS 4,075,406 A    2/1978  Melaja
5,084,104 A    1/1992  Heikkila
(Continued)

FOREIGN PATENT DOCUMENTS

FR    2655661 A1    6/1991
JP    S52 82737 A   7/1977
(Continued)

OTHER PUBLICATIONS

Elina Sjöman, Mika Mänttäri, Marianne Nyström, Hannu Koivikko, Heikki Heikkilä. Nanofiltration of monosaccharide containing solution to recover xylose. Desalination. Nov. 20, 2006. vol. 199. pp. 348-349 (Year: 2006).*

(Continued)

Primary Examiner — Steven A. Friday
(74) Attorney, Agent, or Firm — Craft Chu PLLC; Andrew W. Chu (57) ABSTRACT The method for purifying oses from hemicellulose originating from lignocellulosic biomass includes eliminating the cellulose matrix and the solid residues and/or the suspended materials from the acid hydrolysate containing oses in order to obtain a clarified hydrolysate, and subjecting the clarified hydrolysate, without adding any basic chemical reagent to increase the pH to at least one step of ultrafiltration and/or to at least one step of nanofiltration, so as to obtain a filtrate containing the majority of the pentoses and a retentate containing the species likely to precipitate under the effect of an increase in the pH. The filtrate is treated by at least one step of electrodialysis so as to recover the acid catalyst from (Continued)

an acid-supplemented solution, and obtain a deacidified filtrate.

13 Claims, 4 Drawing Sheets

(51) Int. Cl.
*C13K 1/04* (2006.01)
*B01D 61/02* (2006.01)
*B01D 61/04* (2006.01)
*B01D 61/14* (2006.01)
*B01D 61/16* (2006.01)
*B01D 61/58* (2006.01)
*C08B 37/00* (2006.01)

(52) U.S. Cl.
CPC .......... *B01D 61/145* (2013.01); *B01D 61/16* (2013.01); *B01D 61/422* (2013.01); *B01D 61/58* (2013.01); *C08B 37/0057* (2013.01); *C13K 1/04* (2013.01); *B01D 2311/04* (2013.01); *B01D 2311/06* (2013.01); *B01D 2311/2623* (2013.01); *B01D 2311/2626* (2013.01); *B01D 2311/2642* (2013.01); *B01D 2311/2676* (2013.01)

(56) References Cited

U.S. PATENT DOCUMENTS

| | | | |
|---|---|---|---|
| 6,239,271 | B1 | 5/2001 | Rabbani |
| 6,331,236 | B1* | 12/2001 | Mani ............... B01D 61/44 204/525 |
| 2005/0056600 | A1 | 3/2005 | Ranney |
| 2005/0244934 | A1* | 11/2005 | Foody ............... B01B 1/005 435/101 |
| 2008/0182305 | A1* | 7/2008 | Foody ............... C12P 7/54 435/140 |
| 2009/0056707 | A1* | 3/2009 | Foody ............... B01J 39/04 127/46.2 |
| 2009/0162892 | A1* | 6/2009 | Pompejus ............ C12P 7/46 435/67 |
| 2009/0173339 | A1* | 7/2009 | Heikkila ............ B01D 61/027 127/55 |
| 2009/0270609 | A1* | 10/2009 | Heikkila ............ B01D 61/027 536/127 |
| 2011/0210001 | A1* | 9/2011 | Xu ................. B01D 61/027 204/537 |
| 2012/0211366 | A1 | 8/2012 | Lee |
| 2014/0209093 | A1* | 7/2014 | Medoff ............. C10L 5/442 127/42 |
| 2014/0284277 | A1* | 9/2014 | Medoff ............. B01J 19/085 210/656 |
| 2015/0140606 | A1* | 5/2015 | Minamino .......... C12P 19/14 435/69.1 |
| 2017/0362618 | A1* | 12/2017 | Nguyen ............. D21C 5/005 |

FOREIGN PATENT DOCUMENTS

| | | |
|---|---|---|
| WO | 2004108739 A2 | 12/2004 |
| WO | 2007/048879 A1 | 5/2007 |
| WO | 2008096971 A1 | 8/2008 |
| WO | 2010/046532 A1 | 4/2010 |

OTHER PUBLICATIONS

Carlos Martin et al.; Acid Prehydrolysis, Alkaline Delignification and Enzymatic Hydrolysis of Rice Hulls; Feb. 2007; Cellulose Chemistry and Technology; vol. 41, Issue 2; pp. 129-135 (Year: 2007).*
Hiroshi Teramura et al.; Glucose content in the liquid hydrolysate after dilute acid pretreatment is affected by the starch content in rice straw; Oct. 2, 2013; Bioresource Technology; vol. 149; pp. 520-524 (Year: 2013).*
Masniroszaime Md Zain et al.; Clarification of Glucose from Cellulose Hydrolysate byUltrafiltration with Polyethersulfone Membrane; 2016; International Journal of Biomass & Renewables; vol. 5, Issue 1; pp. 14-18 (Year: 2016).*
Sjoman, E., et al; "Nanofiltration of monosaccharide containing solution to recover xylose", Desalination, Elsevier, Amsterdam, NL, vol. 199, No. 1-3, Nov. 20, 2006, pp. 348-349.

* cited by examiner

METHOD FOR PURIFYING OSES WITHOUT ADJUSTING PH

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention is related to the field of recovering the hemicellulosic fraction, which is originating from lignocellulosic biomass.

The invention relates more particularly to a method for purifying pentoses, which are sugars forming the hemicellulose, while permitting the acid catalyst to be recycled, the latter being used for hydrolyzing the lignocellulosic biomass and for extracting the cellulose therefrom.

2. Description of Related Art Including Information Disclosed Under 37 CFR 1.97 and 37 CFR 1.98

Traditionally, cellulose is used in the manufacture of materials, for example paper, by the paper industries.

Cellulose can also be converted to bioethanol by the so-called «2nd generation» bioethanol sector.

This sector permits to obtain biofuels from advantageously non-food plant components. In other words, there is no competition between this sector and a use of plants for food, as can be the case with bioethanol produced for example from rape or beet.

In particular, the starting plant components that can be used for obtaining 2nd generation biofuels are, for example, wood, green residues, cereal straw, fodder, forest residues, miscanthus, sugar cane bagasse, etc., the latter corresponding to the fibrous residue of sugar cane once the juice has been extracted therefrom. All these plant components can represent lignocellulosic biomass.

Cellulose is the major component of this lignocellulosic biomass, which can include up to 50% cellulose.

The extraction of cellulose from lignocellulosic biomass is generally carried out by implementing physicochemical techniques. In particular, a step of acid hydrolysis of the lignocellulosic biomass can be performed, which permits to recover a cellulose pulp. An enzymatic hydrolysis of the cellulose is then performed, in order to obtain glucose molecules, and the latter is then transformed into ethanol by fermentation, using yeasts.

In addition to cellulose, lignocellulosic biomass also includes hemicellulose and lignin.

Lignin consists of a macromolecule with a complex structure and high molecular weight.

The chemical structure of lignin is varying. The lignins are more particularly monolignol polymers, and there are at least three different ones: coumaryl alcohol, coniferyl alcohol and sinapyl alcohol. The fraction of each of the monomers in the lignin varies considerably and depends on various factors, such as the plant line, the species, the organ, or also the tissue.

As regards the hemicellulose, of which the lignocellulosic biomass is comprised for about 30 mass %, it is the 2nd major component of the pectocellulosic plant wall after cellulose. The hemicellulose plays a bridging role in this wall, between the cellulose fibers and other components of said wall.

The hemicellulose consists of a branched polysaccharide including different types of oses, unlike cellulose, which is exclusively formed of glucose molecules, and more particularly of D-anhydroglucopyranose units connected to each other by glycosidic bonds $\beta$ (1→4).

As regards the ose monomers, which form the hemicellulose, they may be glucose, xylose, mannose, galactose, rhamnose or also arabinose. The most widely represented monomer within the hemicellulose is xylose.

The hemicellulose is a fibrous molecule, insoluble in water. Mostly comprised of pentoses, it is very slightly fermentable and it is therefore difficult to synthesize biofuels originating from hemicellulose.

Therefore, only the cellulose extracted from lignocellulosic biomass is readily convertible to ethanol.

However, techniques should be provided that permit to recover the hemicellulosic fraction from the lignocellulosic biomass, i.e. the fraction including the hemicellulose, and more particularly the oses, namely the pentoses, which the hemicellulose is partially comprised of.

Indeed, the pentoses, and more specifically the xylose, are of interest at the level of several industrial applications, such as the production of intermediate chemicals for xylitol, surfactants or resins.

The methods for purifying pentoses that are currently implemented at industrial level have changed little since the late 1980s. These methods have namely the disadvantage of being highly water- and chemical reagents-consuming, and they are in addition very polluting.

More precisely, once the acid hydrolysis of the lignocellulosic biomass has been performed in order to recover the cellulose, the reference method used so far to permit a purification of the sugars contained in the acid hydrolysate consists first of all in neutralizing the latter.

The neutralization of the acid hydrolysate is traditionally performed by adding thereto a mineral base such as lime or soda. This neutralization will cause the precipitation of the organic macromolecules, such as the proteins or also the lignin.

The precipitated organic macromolecules, as well as the suspended matters, are then removed by sedimentation or centrifugation. The hydrolysate is then demineralized by chromatography, as described in the patent documents U.S. Pat. Nos. 5,084,104, 6,239,271 and WO 2010/046532, by ion exchange, as described in U.S. Pat. No. 4,075,406, FR 2 655 661 and WO 2004/108739.

Finally, as described in U.S. Pat. No. 5,084,104 and WO 2010/046532, the hydrolysate obtained can be concentrated in order to obtain high-purity xylose crystals.

It can also be considered that the so treated hydrolysate is used for producing xylitol, surfactants, or resins.

However, the major disadvantage of these methods lies in that they are extremely polluting because they lead to rejecting about 90% of the acids used for the hydrolysis of the biomass.

Techniques developed more recently and described in the patent documents WO 2008/096971 and US 2012/0211366 have permitted to show the advantage of the electrodialysis for permitting the demineralization of the hydrolysate, after full or partial neutralization of the latter.

More specifically, patent document US 2012/0211366 relates to a method for producing xylose from a hydrolysate using the electrodialysis.

In this method, after a step of hydrolyzing the plant biomass, the pH of the hydrolysate being obtained, initially of about 0.8 to 1.2, must be adjusted, by adding sodium hydroxide, in order to reach a pH between 1.5 and 2.5. As a result, the acid catalyst loses most of its catalytic power and is not likely to be fully recovered and recycled.

In addition, here the addition of sodium hydroxide results, on the one hand, into an increase of the quantity of salts to be separated during the electrodialysis step and, on the other hand, into a precipitation of the soluble impurities at an acid pH. A clarification step is then necessary in order to eliminate the insoluble suspended matters, using a microfilter.

Anyway, in the methods known from the state of the art, the acid catalyst used in the hydrolysis of the biomass is little or not recycled. Indeed, its neutralization, or the adjustment of the pH to a certain value, requires a certain amount of a base. Therefore, the amount of salts to be separated during the demineralization step is considerably increased.

As a result, the existing methods require, for their implementation, a very large amount of water, energy and chemical reagents. Therefore, large quantities of waste water must be treated afterwards.

The patent document WO 2008/096971 has permitted to demonstrate the interest of using the electrodialysis technique in a method for recovering pentoses.

More particularly, in this document is described a method for producing xylitol from a hydrolysate including namely xylose and arabinose, the starting biomass consisting of tropical fruits.

In the method in question, after a conventional step of acid hydrolysis of the biomass, ions, namely sulfate ions and calcium ions, are precipitated by increasing the pH of the hydrolysate, which then changes from a pH 1 or 2 to a pH that can go up to 7.

However, even after this precipitation step, the hydrolysate is likely to still containing non-precipitated ions. The latter, although they are present in the hydrolysate at a low concentration, may result into the formation of a deposition during the subsequent step of concentration of the products of interest, ultimately resulting into a reduction in yield in the production of xylitol.

The implementation of an electrodialysis technique permits to eliminate the non-precipitated salts while limiting the use of ion-exchange resins, which inevitably requires steps of regenerating said resins, which are expensive in time and in chemical reagents.

However, in the method described herein, like in the other methods provided in the prior art, a step of raising the pH is necessary to remove the macromolecules and certain dissolved ions. Therefore, a large portion of the acid added at the time of the hydrolysis of the biomass is neutralized, which results into the loss of most of its catalytic power.

Moreover, the anionic or cationic membranes used in the electrodialysis technique are very sensitive to clogging and contamination by organic molecules. Therefore, the lifetime and the effectiveness of said membranes are likely to be reduced.

The macromolecules can also precipitate in the electrodialysis module, or stack, when the pH is increased.

Therefore, because of the high cost of the electrodialysis membranes, it is necessary to efficiently remove the components of the hydrolysate likely to precipitate, in order to be capable of implementing the electrodialysis technique at industrial scale.

It has already been mentioned that the macromolecules, in particular the lignin and the proteins, are precipitated by raising the pH of the hydrolysate. The latter, being initially of about 1 at the time of the acid hydrolysis, must be adjusted to a value between 2 and 7, for example by adding lime or a solution of soda to the hydrolysate, which inevitably results into the loss of most of the catalytic power of the acid.

BRIEF SUMMARY OF THE INVENTION

The invention provides the possibility of coping with the various disadvantages of the prior art by providing an innovative method for recovering and purifying the sugars, in particular the pentoses, which are present in an acid hydrolysate of hemicellulose obtained from lignocellulosic biomass.

The method according to the present invention has the advantage of being cheaper and more «durable» than the methods provided so far, in the meaning that the chemical reagents, and namely the acid catalyst used for the hydrolysis of the biomass, are for a large part recycled.

To this end, the present invention relates to a method for purifying oses derived from the hemicellulose originating from lignocellulosic biomasses, said oses being contained in an acid hydrolysate obtained by partial hydrolysis of lignocellulosic biomasses by means of at least one acid catalyst, said acid hydrolysate including in addition a cellulosic matrix, solid residues and/or suspended matters, said method being characterized in that it includes the following steps:
- removing from the acid hydrolysate the cellulosic matrix and the solid residues and/or the suspended matters in order to obtain a clarified hydrolysate;
- without addition of a basic chemical reagent to increase the pH, said clarified hydrolysate is subjected to at least one ultrafiltration step and/or to at least one nanofiltration step, so as to obtain a filtrate containing the majority of the pentoses and a retentate containing the species likely to precipitate under the action of an increase in pH;
- said filtrate is treated by means of at least one electrodialysis step so as to recover the acid catalyst in an acid-enriched solution and to obtain a deacidified filtrate.

According to a peculiarity of the invention, the present method is also characterized in that, prior to the filtration, the cellulosic matrix is removed in a first step and, in a second step, the solid residues and/or the suspended matters.

Advantageously, the solid residues and/or the suspended matters are removed by sedimentation and/or centrifugation and/or filtration on a press and/or filtration on a membrane.

According to a particularly interesting embodiment, the acid catalyst being used consists of sulfuric acid the concentration of which, in the acid hydrolysate, is advantageously between 5 and 50 g/L.

Preferably, the cut-off threshold of the filter used during the filtration step is between 100 and 50 000 Da, preferably between 10 000 and 15 000 Da.

Furthermore, an additional feature of the present method is defined by the fact that during the electrodialysis step acidified water is introduced into the compartments of the electrodialysis apparatus where the acid is concentrated, so to have a conductivity higher than or equal to 5 mS/cm.

The present invention also provides that after the electrodialysis step said deacidified filtrate can also be demineralized by electrodialysis and/or by chromatography and/or by ion exchange.

Advantageously, said oses are pentoses, preferably xylose and/or arabinose.

The present purification method is also characterized in that, following the step of demineralization of the deacidified filtrate, the xylose is purified by concentration of the deacidified and demineralised filtrate, then by crystallization.

According to the invention, it can also be provided that following the crystallization step, after which a sweet liquor comprising xylose and at least another ose is obtained, a separation step is performed in order to separate the xylose from the other ose or oses.

In this case, the separation of the xylose and the other ose or oses can be performed by crystallization, by ligand-exchange chromatography, which may or may not be combined with crystallization.

The present invention includes many advantages.

On the one hand, the method permits, without any neutralization of the acid catalyst by means of a basic reagent, to eliminate almost all the organic molecules, such as the lignins or the proteins. These molecules are then no longer likely to intervene in the rest of the method, namely by clogging or contaminating the ionic membranes, or to precipitate when the pH inevitably increases during the electrodialysis step. Thus, unlike in the existing methods, the electrodialysis membranes have an improved lifetime, which permits to consider a transposition of the method according to the invention at an industrial level.

On the other hand, the present purification method has the advantage of permitting to recover, by electrodialysis, the acid catalyst that is used for the hydrolysis of the lignocellulosic biomass. As a result, the recycled acid catalyst can advantageously be re-used in a subsequent method for purifying oses. In addition, the acid concentration can readily be readjusted before its re-use as a biomass hydrolysis catalyst.

On the other hand, the yields of purification of the oses, and namely of the pentoses, obtained with the present method, are very similar to the yields of the methods traditionally used in the state of the art.

Therefore, at equal purification performances as the conventional methods, the present method permits a reduction in water consumption. The use of chemical reagents, namely of acid catalyst, but also of basic compound, such as lime or soda, which is essential in the conventional methods for the acid neutralization step, is also reduced. This results into a reduction of the operating costs. In addition, the environmental impact of the step of purification of the oses, namely pentoses, is considerably reduced.

The method according to the invention is therefore of particular interest within the framework of the development of lignocellulosic biomass recovery projects that are both profitable and respectful of the principles of sustainable development.

BRIEF DESCRIPTION OF THE SEVERAL VIEWS OF THE DRAWINGS

Further features and advantages of the invention will become clear from the following detailed description of non-restrictive embodiments of the invention, with reference to the attached drawings.

DETAILED DESCRIPTION OF THE INVENTION

Figure 1:
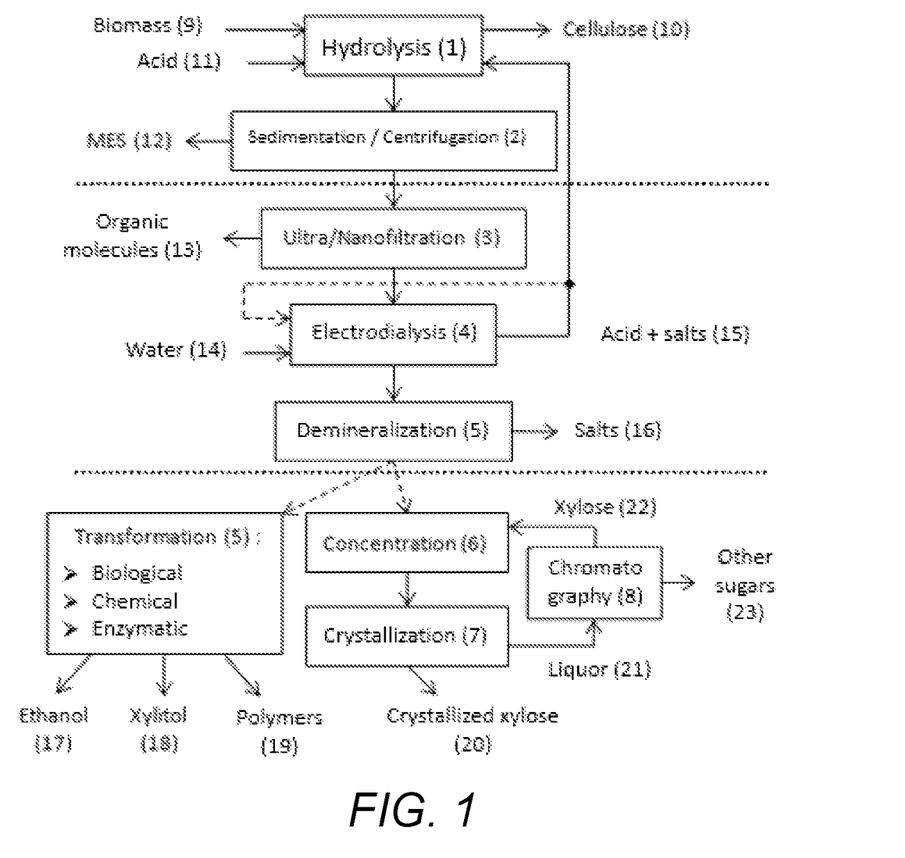
FIG. 1 is a diagram that schematically shows various steps implemented in a preferred embodiment of the method for purifying the oses according to the invention.

As shown in FIG. 1, the present invention relates to a method for purifying oses. Initially, these oses are contained in lignocellulosic biomasses 9, within complex macromolecules the latter are comprised of.

The starting lignocellulosic biomasses in the present method may include any kind of plant components. Thus, the starting biomasses 9 may advantageously be comprised of at least one component chosen from wood, green residues, cereal straws, fodder, forest residues, miscanthus, sugar cane bagasse and the like.

More particularly, the oses, which are purified by implementing the method according to the invention, are oses, which are part of the hemicellulose, the latter being one of the three main components of the lignocellulosic biomasses, with cellulose and lignin.

The hemicellulosic fraction from which these oses originate is derived from the partial hydrolysis 1 of lignocellulosic biomasses 9, said hydrolysis 1 being performed by bringing said biomasses 9 into contact with at least one acid catalyst 11.

Said acid catalyst 11 being used to perform the hydrolysis step 1 consists, according to a particular but non-restrictive embodiment, of sulfuric acid with the chemical formula $H_2SO_4$.

Preferably, the sulfuric acid $H_2SO_4$ has a mass concentration varying between 5 and 50 g/L, preferably between 10 and 20 g/L, and yet more preferably a concentration equal to 15 g/L, in the acid hydrolysate, or reaction medium.

However, any other kind of acid catalyst capable of permitting the hydrolysis of lignocellulosic biomasses can be used.

The primary purpose of the acid catalysis step 1 is to permit the recovery of a cellulose pulp 10 from an acid hydrolysate including namely, in addition, solid residues and/or suspended matters. As regards the cellulose pulp 10, also referred to as cellulose matrix, it is used subsequently namely in the paper industry or for the manufacture of 2nd generation biofuel, for example bioethanol.

Following the acid hydrolysis 1, and after removal of the cellulose 10, the solid residues and/or the suspended matters, is obtained a clarified acid hydrolysate particularly rich in oses, and namely in pentoses, resulting from the hydrolysis of the hemicellulose macromolecule. The pentoses are oses, or monosaccharides, which have 5 carbon atoms and have the raw formula $C_5H_{10}O_5$. The hemicellulose is namely comprised of arabinose and especially of xylose, which are both aldopentoses, i.e. they include an aldehyde function in position 1.

However, it has already been mentioned that the hemicellulose is also formed of other oses, such as glucose, mannose, galactose and rhamnose. These oses are all hexoses, of the formula $C_6H_{12}O_6$, and can also be dissolved in the acid hydrolysate.

It can be considered to simultaneously eliminate from said acid hydrolysate, by means of a single filtration step, the cellulosic matrix 10, the solid residues and/or the suspended matters, so as to obtain a clarified hydrolysate.

In another embodiment, the cellulosic matrix is removed in a first step by simply removing it from the acid hydrolysate, then, in a second step, the solid residues and/or the suspended matters present in the acid hydrolysate are removed.

This removal of the solid residues and/or the suspended matters is advantageously performed by implementing a treatment by sedimentation and/or centrifugation and/or by filtration on a press and/or filtration on a membrane, whereby the latter may consist of a microfiltration or an ultrafiltration.

Such a step permits to eliminate the solid residues and/or the suspended matters 12, or MES, originating for example from the starting plant components and which could eventually still be present in the acid hydrolysate. A hydrolysate clarified from all solid residues and all MES is then obtained.

In the continuation of the method, and as illustrated in the attached FIG. 1, at least one ultrafiltration step and/or at least one nanofiltration step 3 is performed on the clarified acid hydrolysate. The aim of this step is to remove, in acidic conditions, without any modification of the pH, the macromolecules likely to precipitate when the pH will inevitably be increased during a subsequent step of the method.

This filtration step permits to obtain, on the one hand, a filtrate, which corresponds to the liquid recovered at the exit of the filtration and, on the other hand, a retentate corresponding to the fraction retained at the level of the filter.

The carrying out of such a filtration treatment 3 of said clarified acid hydrolysate has the substantial advantage of promoting the removal of organic molecules, such as lignin or other proteins, which are found in the retentate. In addition, this removal is advantageously carried out without any addition of basic chemical reagent to increase the pH and to cause a precipitation of said molecules. Thus, the acid catalyst is not neutralized and can subsequently be recovered for re-use, because its catalytic power is completely preserved. Indeed, said catalyst is found at the level of the filtrate, the latter also containing, inter alia, the oses originating from hemicelluloses, which must be purified.

Preferably, the ultrafiltration and/or nanofiltration step is carried out by means of a membrane, or filter, having a cut-off threshold between 100 and 50 000 Da, and yet more preferably between 10 000 and 15 000 Da.

The ultrafiltration membranes and/or the nanofiltration membranes being used in the present method are advantageously organic membranes, which have been carefully selected for their resistance to an acidic pH of about 1 and for permitting a selective removal of the soluble impurities at the pH of the hydrolysis.

The aforementioned cut-off thresholds indeed advantageously permit an optimal removal of most of the organic molecules, which are likely to precipitate when the pH is subsequently increased.

Indeed, since the latter are likely to contaminate ionic membranes used subsequently in the method, even to precipitate during the next electrodialysis step, it is particularly important to remove the largest possible proportion of these molecules.

After the filtration step is thus performed a step of filtrate treatment by an electrodialysis technique 4, which advantageously permits to recover the major part of the acid catalyst 11 that has been used to hydrolyze the lignocellulosic biomass 9.

More specifically, said acid catalyst 11 is recovered, during the electrodialysis step 4, in an acid-enriched solution 15, and also including salts, also referred to as «brine».

Following this electrodialysis step 4, the filtrate that has been cleared of the acid is also recovered, which is therefore referred to as deacidified filtrate in the continuation of the description.

The electrodialysis technique permits an extraction of ions present in a solution. It is carried out by means of an electrodialyzer, or electrodialysis cell, comprised of a plurality of compartments separated by anionic and cationic membranes. Generally, the electrodialyzer comprises an alternation of anionic and cationic membranes, forming multiple electrodialysis cells, which are positioned between two electrodes permitting the migration of the ions under the action of a difference in electrical potential.

The anionic membranes include resins with positively charged cation groups permitting the passing through of the anions of the solution, which can penetrate into the membrane and replace the anions initially present at the level of the membrane. Conversely, the cationic membranes are formed of negatively charged anionic groups, thereby permitting the penetration of the cations and to repel the anions under the action of the electric field.

The cations, which migrate in the direction of the electric current towards the negatively charged cathode, leave the first compartment through the cationic membrane and are blocked in a second compartment by the anionic membrane.

The negatively charged anions also leave the first compartment by migrating through the anionic membrane to the positively charged anode. They are then blocked in a second compartment by the cationic membrane.

As a consequence, the first compartment sees its salt concentration decreasing. This is why it is referred to as the dilution compartment. On the contrary, in the second compartment the concentration of dissolved ions increases; it is a so-called concentration compartment («brine» compartment).

The electrodialysis apparatus thus includes an alternation of dilution compartments and concentration compartments.

The acid catalyst 11 can then be recovered in the concentration compartments of the electrodialyzer. More specifically, and as already mentioned above, an acid-enriched solution 15 is recovered, which in addition to the acid catalyst also includes salts, said solution 15 also being referred to as «brine».

In order to be able to recycle the acid catalyst during the first step of hydrolysis 1 of the lignocellulosic biomass 9, the acid-enriched solution 15 must reach a sufficient concentration of acid. To this end, said solution 15 may again be subjected to at least one electrodialysis step 4, symbolized by the dotted arrow in the diagram of FIG. 1.

In other words, the brine 15 is not renewed between two electrodialysis steps, while a new filtrate, including a certain concentration of acid catalyst and pentoses to be purified, is treated by electrodialysis, so as to simulate a counter-current.

Thus, by means of the electrodialysis, it can be considered, on the one hand, to recycle the acid catalyst, but also, on the other hand, to readjust its concentration in order to prepare its recycling with a view to a new step of hydrolysis of lignocellulosic biomass.

In order to adjust the acid concentration, it can also be considered to control the volumes of liquid implemented during the electrodialysis, namely, on the one hand, the volume of filtrate to be treated and, on the other hand, the volume of electrodialysis solution, or water 14.

In a preferred example, the water 14, which is initially introduced into the compartments where the acid concentrates, i.e. the concentration compartments, must be slightly acidified in order to have a sufficient conductivity, higher or equal to 5 mS/cm. Indeed, the electrodialysis method is based on the transport of ions through the membranes by means of an electric field; this assumes that the circulating solutions are conductive.

Preferably, said water 14 has a pH between 1.5 and 2.5, and yet more preferably of about 2. This water 14 or «brine» may namely consist of a solution of sulfuric acid having a mass concentration between 0.25 and 1 g/L, preferably of about 0.5 g/L.

Advantageously, during the electrodialysis 4, the pH is monitored in the various dilution and concentration compartments of the electrodialysis apparatus. Thus, this monitoring permits an optimization of the treatment by electrodialysis. This monitoring permits in addition to identify the point at which most of the starting acid catalyst 11 has been recovered, but with as few salts as possible.

Following the electrodialysis step, a demineralization 5 of the deacidified filtrate is carried out, so as to eliminate a substantial proportion of salts 16, which could still be contained in said filtrate.

The demineralization step 5 may be of different kinds, depending on the subsequent way of recovering chosen to recover the oses originating from the hemicellulosic fraction, in particular the pentoses.

More particularly, the deacidified filtrate is demineralized by means of at least one technique chosen from electrodialysis, chromatography and ion exchange.

In other words, it can be considered to implement either one of these techniques, or also to use a combination of several of these techniques, so as to obtain a filtrate that is both deacidified and demineralized rich in oses, and namely in pentoses, derived from the hemicellulose.

The implemented demineralization technique(s) depend(s) on the way of recovering the oses, which will be chosen later, as mentioned above, but also on the nature of the salts being present (mineral or organic, monovalent or divalent salts) and their concentration. This will permit to minimize the consumption of water, energy, and also chemical reagents.

In a preferred exemplary embodiment, a demineralization step by electrodialysis or by chromatography is advantageously implemented to remove a significant proportion of salts 16 from the deacidified filtrate. The ion exchange will be better adapted as a final treatment in order to eliminate the traces of salts that could remain.

Following the demineralization step, the deacidified and demineralized filtrate rich in oses, namely in pentoses, can be recovered in various ways.

One of the pentoses present in said filtrate, xylose, may be subjected to a transformation 5, whereby the latter may be biological, chemical or enzymatic, so as to permit the production of xylitol 18 or also intermediate chemicals, surfactants, or polymers 19.

For these applications, it is necessary to separate the sugars from each other in order to obtain a pure xylose solution. Obtaining this solution is feasible, for example, by carrying out a ligand-exchange chromatography, a crystallization or a combination of these two techniques.

In another equally advantageous exemplary embodiment, the xylose is purified and extracted from the filtrate in solid form 20, by concentration 6 of said filtrate, followed by a crystallization step 7 in order to obtain crystallized xylose 20. Following this crystallization step 7, a sweet liquor 21 is also obtained, which can optionally be subjected to a ligand-exchange chromatography step 8 in order to recover the xylose 20 likely to be contained in said liquor 21 by separating them from the other sugars 23.

Such a step advantageously permits to optimize the yield of the method for extracting xylose from the hemicellulose initially contained in the biomass 9.

The interest of the method according to the invention for purifying oses, namely pentoses, is illustrated in the example below in connection with FIGS. 2 and 3 attached to the present application.

Example: Purification of a Hydrolysate of Wheat Bran Obtained after Hydrolysis of Diluted Sulfuric Acid Table 1 below shows the characteristics of the wheat-bran hydrolysate, which was studied after a step of hydrolysis of the wheat bran by means of a solution of diluted sulfuric acid ($H_2SO_4$) at a mass concentration equal to 15 g/L.

TABLE 1

| Composition of the acid hydrolysate | | | | | | | |
|---|---|---|---|---|---|---|---|
| MS % | pH | Conductivity (mS/cm) | MES (g/L) | OD to 420 nm | $H_2SO_4$ (g/L) | Glucose (g/L) | Xylose (g/L) | Arabinose (g/L) |
| 8.2 | 1.2 | 34.5 | 1.5 | 2.2 | 11.5 | 9 | 18 | 8 |

In this table, MS represents the mass fraction of the sum of the substances in solution or suspended in the hydrolysate, OD at 420 nm represents the optical density, or absorbance, measured at a wavelength of 420 nm and MES Represents the suspended matters.

Prior to proceeding to the purification of the hydrolysate, the latter is subjected to a centrifugation step in order to remove the suspended matters. After centrifugation, the solid residue pellet obtained represents approximately 10% of the centrifuged volume.

The supernatant obtained is ultrafiltered at a temperature of 40° C. with an Alfa Laval UFX10 organic polysulfone on polypropylene organic membrane resistant to the acidic pH and having a cutoff threshold of 10 000 Da (or 10 kDA) and with a transmembrane pressure of about 6 bars.

The characteristics of the supernatant (initial hydrolysate), of the retentate, and the permeate, or filtrate, were measured and are shown in Table 2 below.

TABLE 2

Composition after ultrafiltration of the acid hydrolysate

|  | Volume (L) | Brix (°B) | pH | Conductivity (mS/cm) | MES at pH 5 (g/L) | OD at 420 nm |
|---|---|---|---|---|---|---|
| Initial hydrolysate | 8 | 8.2 | 1.2 | 34.5 | 3.6 | 2.2 |
| Final retentate | 1.8 | 11.6 | 1.4 | 30.2 | — | 6.5 |
| Final Permeate | 6.2 | 7.0 | 1.3 | 34.5 | 0.0 | 0.5 |

A substantial decrease was observed in the final permeate (or filtrate) of the absorption at 420 nm (OD). The latter represents the presence of the organic coloring macromolecules. The decrease in OD at 420 nm therefore represents the elimination of these macromolecules in the permeate.

In addition, the amount of suspended matters (MES) was measured at pH 5 before and after the ultrafiltration step, said pH having been adjusted by adding a soda solution on a sample solution. The results shown in Table 2 show the quantitative elimination of these molecules, which would have been likely to precipitate during the subsequent electrodialysis step. Indeed, in the final permeate, there is no longer any trace of suspended matter (0.0 g/L).

The possibility of carrying out the ultrafiltration step by means of a filter having a cut-off threshold of less than 10 000 Da has already been mentioned. However, the results show that, in this example, this cut-off threshold is sufficient to effectively eliminate the suspended matters and the organic macromolecules, in order to thus durably preserve the performance of the electrodialyzer membranes and to prevent the precipitation of organic compounds within the compartments of the latter.

In the next step, a conventional two-compartment electrodialysis pilot was used to recover most of the acid catalyst, the sulfuric acid (H2SO4). The characteristics of the pilot are summarized in Table 3 below.

TABLE 3

Characteristics of the electrodialysis pilot EUR2-10

| Anionic Membranes | AMX-Sb |
|---|---|
| Cationic Membranes | CMX-Sb |
| Surface Area | 200 cm$^2$ |
| Brine | H$_2$SO$_4$ à 0.5 g/L |
| Electrolyte | NaCl |
| Voltage | 12 V |

Two electrodialysis phases were conducted. The results obtained after these two phases are given in Table 4 below.

The brine obtained after the 1st electrodialysis phase was recycled during the 2nd phase, in order to reach the acid concentration necessary for it to be recycled in a new method for hydrolysis of the lignocellulosic biomass; this acid concentration is set between 10 and 20 g/L.

1st Electrodialysis Phase

After the ultrafiltration step mentioned above, a volume of 2 L of hydrolysate, or filtrate, was treated with 2 L of so-called «fresh» brine having a sulfuric acid concentration of 0.5 g/L. The use of such a brine having a conductivity higher than 5 mS/cm facilitates the electrodialysis step.

Figure 2A:
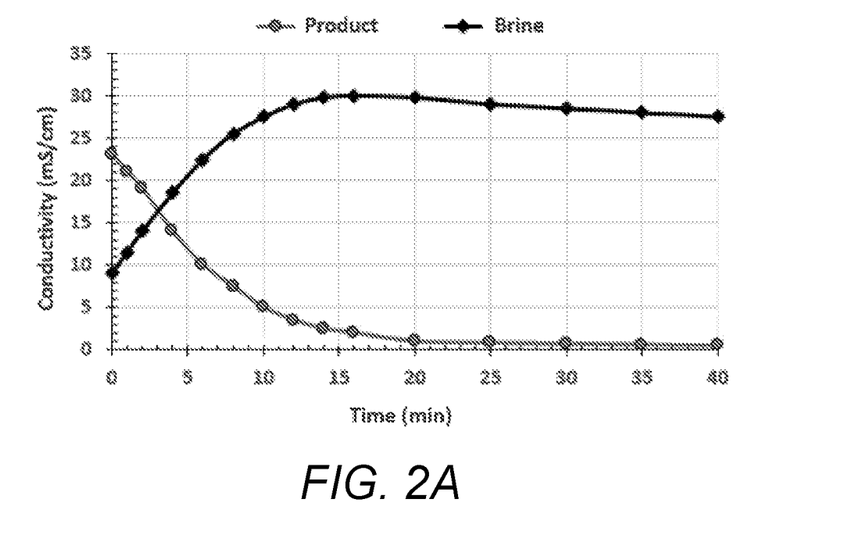
FIGS. 2A, 2B and 2C are graphs illustrating respectively the evolution of the pH, the conductivity (in mS/cm) and the intensity (in A) depending on the time (in min) during a first electrodialysis phase with 2 L of filtrate, corresponding to the hydrolysate having been subjected to an ultrafiltration step with a membrane with a porosity equal to 10 000 Da and 2 L of "fresh" brine corresponding to a solution of sulfuric acid H2SO4 at a mass concentration equal to 0.5 g/L.
Figure 2B:
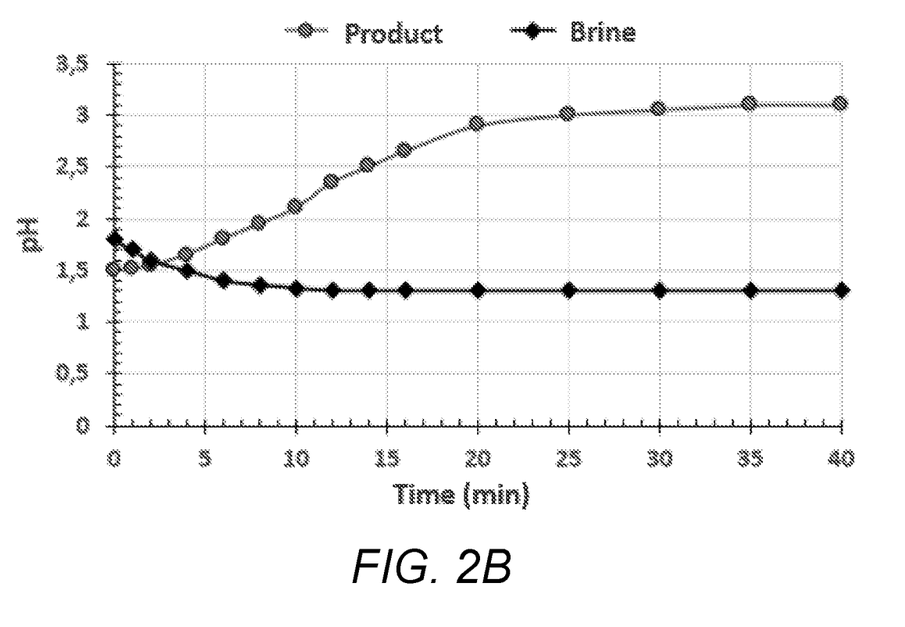
Figure 2C:
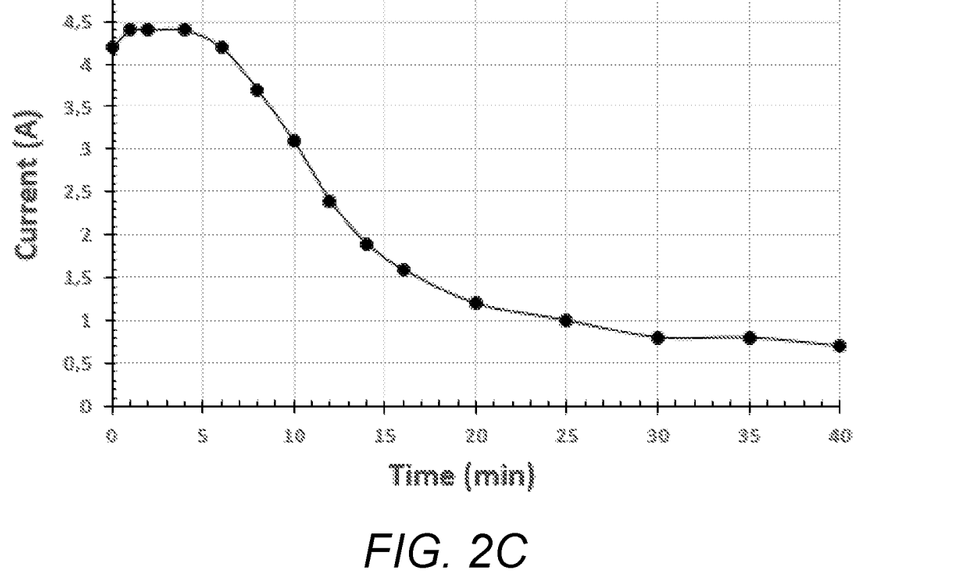

The evolution of the pH, of the conductivity and of the current intensity depending on the time are represented respectively in the attached FIGS. 2A, 2B and 2C.

The results obtained show that the product was largely demineralized after a duration of about 20 minutes of electrodialysis; indeed, after 20 min, it is observed in FIG. 2A that the residual conductivity in the product is less than 1 mS/cm. This results in addition into a drop in the current intensity.

The results in Table 4 below show that after 20 minutes of electrodialysis, more than 90% of the sulfuric acid was transferred into the brine. As regards the sugars, more than 98% remained in the product.

Therefore, it is not necessary to process the product for more than 20 min.

The brine finally reaches a pH equal to 1.3 and its acid content is about 0.12 eq/L, i.e. a concentration of sulfuric acid H$_2$SO$_4$ of 5.9 g/L.

TABLE 4

Composition of products at the end of the electrodialysis

|  | Volume (L) | Brix (°B) | pH | Conductivity (mS/cm) | H$_2$SO$_4$ (g/L) | Glucose (g/L) | Xylose (g/L) | Arabinose (g/L) |
|---|---|---|---|---|---|---|---|---|
| Product 1$^{st}$ ED | 2 | 5.5 | 3.1 | 0.5 | 0.8 | 7.5 | 15.4 | 7.3 |
| Brine 1$^{st}$ ED | 2 | 1.4 | 1.3 | 27.1 | 5.9 | 0.1 | 0.2 | 0.1 |
| Product 2$^{nd}$ ED | 2.2 | 5.6 | 2.8 | 0.9 | 1.5 | 7.4 | 15.4 | 7.3 |
| Brine 2$^{nd}$ ED | 1.2 | 3.9 | 1.0 | 60.0 | 14.2 | 0.0 | 0.4 | 0.2 |

2nd Phase of Electrodialysis

A volume equal to 1.2 L of previous brine is used with 2.2 L of ultrafiltered hydrolysate. The evolution of the pH, of the conductivity and of the current intensity depending on the time are represented respectively in FIGS. 3A, 3B and 3C.

Figure 3A:
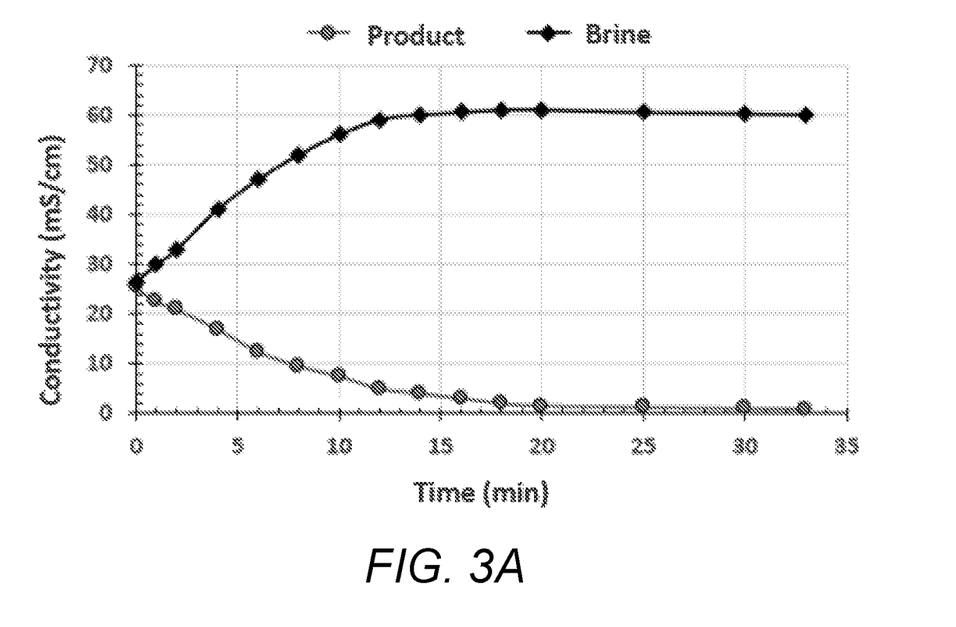
FIGS. 3A, 3B and 3C are graphs illustrating respectively the evolution of the pH, the conductivity (in mS/cm) and the intensity (in A) depending on the time (in min) during a second electrodialysis phase with 2.2 L of filtrate, corresponding to the hydrolysate having been subjected to an ultrafiltration step with a membrane with a porosity equal to 10 000 Da and 1.2 L of brine recovered after the first electrodialysis phase.
Figure 3B:
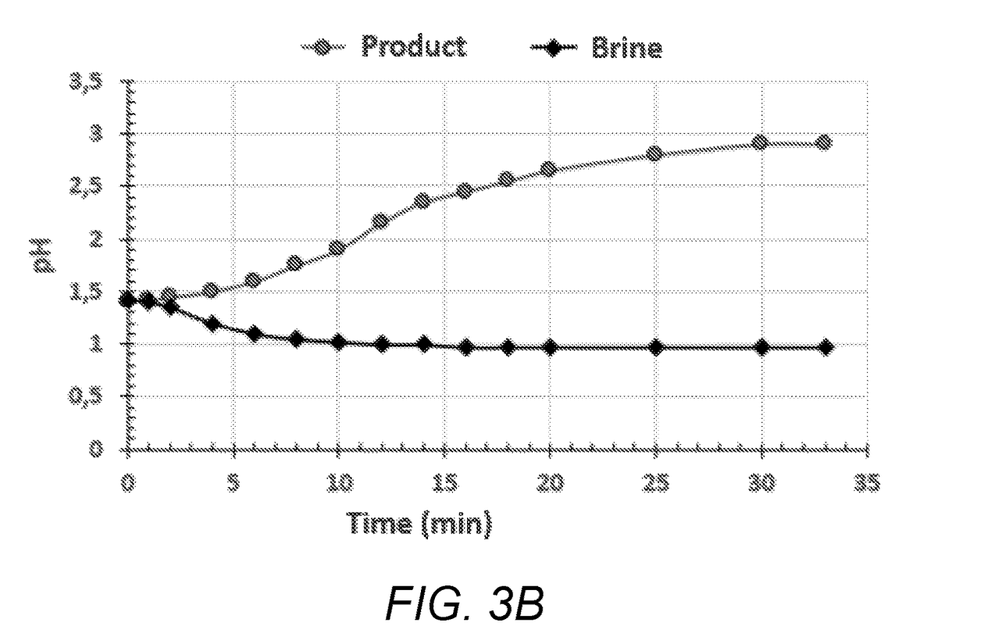
Figure 3C:
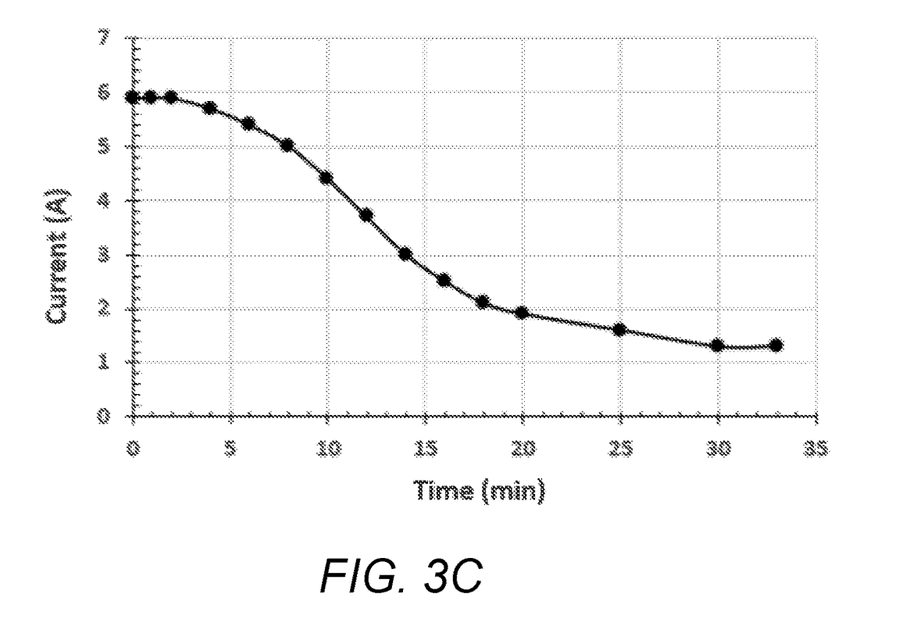

Again, the product was demineralized after 20 minutes of electrodialysis, the residual conductivity being less than 1 mS/cm. Therefore, a duration of 20 min is sufficient to transfer more than 90% of the sulfuric acid into the brine and to retain more than 98% of the sugar in the product.

After the 2nd electrodialysis phase, the brine has reached a pH close to 1 and its acid content is about 0.29 eq/L, i.e. a concentration of sulfuric acid H2SO4 of 14.2 g/l.

Therefore, the brine has a sulfuric acid concentration sufficient to be recycled during the step of hydrolysis of the lignocellulosic biomass.

Finally, a finishing treatment by means of ion exchange is carried out to remove the last traces of salts and acids. The product deriving from the 2nd electrodialysis is introduced at 3.6 BV/h («bed volume» per hour) into two columns mounted in series, each containing a strong cationic resin (LEWATIT S2528) and a weak anionic resin (LEWATIT S4328).

In total, up to 30 BV of product could be processed at room temperature before one of the two resins was saturated.

If a comparison is made with the reference method, in which a partial or complete neutralization of the hydrolysate is performed, it is thus possible to treat at each cycle at least 10 times more products. Therefore, it is possible, with the method according to the invention, to save water and the corresponding chemical reagents.

This treatment has permitted to divide by 5 the conductivity of the product (this being ultimately 0.17 mS/cm) and therefore its salt content.

Finally, a finishing treatment per mixed and activated-carbon bed has permitted to obtain a demineralized pentose solution with a conductivity of less than 10 µS/cm and perfectly discolored.

Of course, the invention is not limited to the examples illustrated and described above, which may have variants and modifications without departing from the scope of the invention.

We claim:

1. A method for purification, the method comprising the steps of:
    reacting lignocellulosic biomasses and at least one acid catalyst so as to form an acid hydrolysate, a cellulosic matrix, solid residues and suspended matters;
    removing said cellulosic matrix, said solid residues and said suspended matters from said acid hydrolysate so as to obtain a clarified hydrolysate;
    filtering said clarified hydrolysate, without any addition of a basic chemical reagent to increase pH so as to obtain a filtrate and a retentate,
    wherein the step of filtering is selected from a group consisting of ultrafiltration and nanofiltration,
    wherein said filtrate is comprised of said at least one acid catalyst and a plurality of oses, and
    wherein said retentate is comprised of organic molecules, said organic molecules being reactive to an increase in pH; and
    treating said filtrate with electrodialysis so as to separate said at least one acid catalyst in an acid-enriched solution from said oses and so as to obtain said oses in a deacidified filtrate.

2. The method for purification, according to claim 1, wherein the step of removing said cellulosic matrix, said solid residues and said suspended matters is comprised of the steps of:
    removing said cellulosic matrix; and
    removing said solid residues and said suspended matters after the step of removing said cellulosic matrix.

3. The method for purification, according to claim 2, wherein the step of removing said solid residues and said suspended matters is comprised of at least one of a group consisting of: sedimentation, centrifugation, filtration on a press, and filtration on a membrane.

4. The method for purification, according to claim 1, wherein said at least one acid catalyst is comprised of sulfuric acid, and wherein a concentration of said at least one acid catalyst in said acid hydrolysate is between 5 and 50 g/L.

5. The method for purification, according to claim 1, wherein the step of filtering is comprised of filtering with a filter having a cut-off threshold between 100 and 50 000 Da.

6. The method for purification, according to claim 5, wherein the step of filtering is comprised of filtering with said filter having said cut-off threshold between 10,000 and 15,000 Da.

7. The method for purification, according to claim 1, wherein the step of treating said filtrate with electrodialysis comprises the step of:
    introducing acidified water into compartments of an electrodialysis apparatus so as to concentrate said at least one acid catalyst in said acid-enriched solution, said acid-enriched solution having a conductivity higher than or equal to 5 mS/cm.

8. The method for purification, according to claim 1, further comprising the step of:
    demineralizing said deacidified filtrate by at least one of a group consisting of electrodialysis, chromatography, and ion exchange so as to obtain oses and demineralization salts.

9. The method for purification, according to claim 1, wherein said oses are comprised of pentoses.

10. The method for purification, according to claim 9, wherein said pentoses are comprised of at least one of a group consisting of: xylose and arabinose.

11. The method for purification, according to claim 10, wherein said pentoses are comprised of xylose, the method further comprising the steps of:
    demineralizing said deacidified filtrate so as to obtain oses and demineralization salts;
    removing said demineralization salts from said oses;
    concentrating said oses; and
    crystallizing said oses so as to obtain said xylose.

12. The method for purification, according to claim 11, wherein the step of crystallizing said oses further comprises the steps of:
    forming a sweet liquor being comprised of xylose and at least another ose; and
    separating said xylose from said at least another ose.

13. The method for purification, according to claim 12, wherein the step of separating said xylose is comprised of at least one of a group consisting of: crystallization and a ligand-exchange chromatography.

* * * * *